United States Patent
Yabe et al.

(10) Patent No.: US 9,389,196 B2
(45) Date of Patent: Jul. 12, 2016

(54) WATER-CONCENTRATION DETECTION DEVICE

(75) Inventors: Tatsuya Yabe, Tokyo (JP); Yoshiyuki Tamura, Tokyo (JP); Chieko Nishida, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 538 days.

(21) Appl. No.: 13/984,259

(22) PCT Filed: Apr. 2, 2012

(86) PCT No.: PCT/JP2012/059008
§ 371 (c)(1),
(2), (4) Date: Aug. 7, 2013

(87) PCT Pub. No.: WO2012/137745
PCT Pub. Date: Oct. 11, 2012

(65) Prior Publication Data
US 2013/0319111 A1    Dec. 5, 2013

(30) Foreign Application Priority Data

Apr. 7, 2011 (JP) .................................. 2011-085344
May 25, 2011 (JP) .................................. 2011-116634
Sep. 5, 2011 (JP) .................................. 2011-193182

(51) Int. Cl.
*G01N 27/12* (2006.01)
*G01N 27/48* (2006.01)

(52) U.S. Cl.
CPC ................................ *G01N 27/121* (2013.01)

(58) Field of Classification Search
CPC ....... G01N 27/02; G01N 27/06; G01N 27/12; G01N 27/48; G01N 27/121
See application file for complete search history.

(56) References Cited

U.S. PATENT DOCUMENTS

| 2002/0022787 A1* | 2/2002 | Takehara | A61B 5/0537 600/547 |
| 2003/0169054 A1* | 9/2003 | Rynhart | G01N 27/233 324/649 |
| 2011/0094883 A1* | 4/2011 | Ito | G01N 27/4077 204/429 |

* cited by examiner

*Primary Examiner* — Susan D Leong
(74) *Attorney, Agent, or Firm* — Buchanan Ingersoll & Rooney PC

(57) ABSTRACT

The water-concentration detection device for detecting a water concentration of insulating gas filled in a gas-insulated device includes: porous electrodes having porous properties that are arranged to face each other in the insulating gas; a solid electrolyte membrane that is sandwiched between and fixedly attached to the electrodes and has hydrogen-ion conductivity; a voltage application unit that applies an alternating-current voltage at a frequency of 325 Hz or a frequency of 10 Hz or lower to the electrodes; an impedance measurement unit that measures an alternating-current impedance between the electrodes in a state in which the alternating-current voltage is applied to the electrodes; and a water-concentration detection unit that detects the water concentration of the insulating gas based on the alternating-current impedance measured by the impedance measurement unit.

9 Claims, 10 Drawing Sheets

WATER-CONCENTRATION DETECTION DEVICE

FIELD

The present invention relates to a water-concentration detection device that detects a concentration of water in insulating gas filled in a gas-insulated device.

BACKGROUND

A gas-insulated device is filled with insulating gas such as $SF_6$ gas. In a conventional water-concentration detection device present in $SF_6$ gas, a water sensor that detects water is installed in a gas-insulated device. This water sensor is configured to include porous electrodes provided to face each other and a hydrogen-ion conductive solid electrolyte membrane that is provided between the porous electrodes and in equilibrium with the water concentration of $SF_6$ gas. This water-concentration detection device measures a water concentration of $SF_6$ gas by applying an alternating-current (AC) voltage to the porous electrodes and measuring inter-electrode AC impedance changing correspondingly to the water concentration of the $SF_6$ gas (see Patent Literature 1 and Non Patent Literature 1).

CITATION LIST

Patent Literature

Patent Literature 1: Japanese Patent Application Laid-open No. 2006-308502

Non Patent Literature

Non Patent Literature 1: "Moisture Detection of $SF_6$ Gas Instruments by Solid Electrolyte", IEEJ National Convention, 2005, 3-171

SUMMARY

Technical Problem

As described above, because the AC voltage is applied to the porous electrodes, the measurement accuracy of the water-concentration detection device for measuring the water concentration has occasionally degraded under the influence of frequency components of a frequency of 50 Hz or 60 Hz that is the frequency of a commercial power supply and/or frequency components that are harmonics of these frequency components.

The present invention has been achieved in view of the above-mentioned circumstances, and an object of the present invention is to provide a water-concentration detection device that can minimize the influence of frequency components of a commercial power supply and frequency components that are harmonics of these frequency components and measure a water concentration with high accuracy.

Solution to Problem

In order to solve the above-mentioned problems and achieve the object, the present invention provides a water-concentration detection device for detecting a water concentration of insulating gas filled in a gas-insulated device, the water-concentration detection device comprising: porous electrodes that are arranged to face each other in the insulating gas; a solid electrolyte membrane that is sandwiched between and fixedly attached to the electrodes, and has hydrogen-ion conductivity; a voltage application unit that applies an alternating-current voltage to the electrodes at a frequency of 325 Hz or a frequency equal to or lower than 10 Hz; an impedance measurement unit that measures an alternating-current impedance between the electrodes in a state in which the alternating-current voltage is applied to the electrodes; and a water-concentration detection unit that detects a water concentration of the insulating gas based on the alternating-current impedance measured by the impedance measurement unit.

Advantageous Effects of Invention

According to the present invention, as an advantageous effect, it is possible to measure a water concentration with high accuracy while minimizing the influence of frequency components of a commercial power supply and frequency components that are harmonics thereof by applying an AC voltage at a frequency of 325 Hz or a frequency equal to or lower than 10 Hz to electrodes.

Furthermore, it is possible to make applied components and products commonalized so that the manufacturing cost of the water-concentration detection device can be held down because there is no need to change a frequency for the AC voltage to be applied from a voltage application unit depending on regions or countries where the water-concentration detection device is used.

DESCRIPTION OF EMBODIMENTS

Water-concentration detection devices of embodiments according to the present invention will be explained below in detail with reference to the drawings. The present invention is not limited to the embodiments.

First Embodiment

Figure 1:
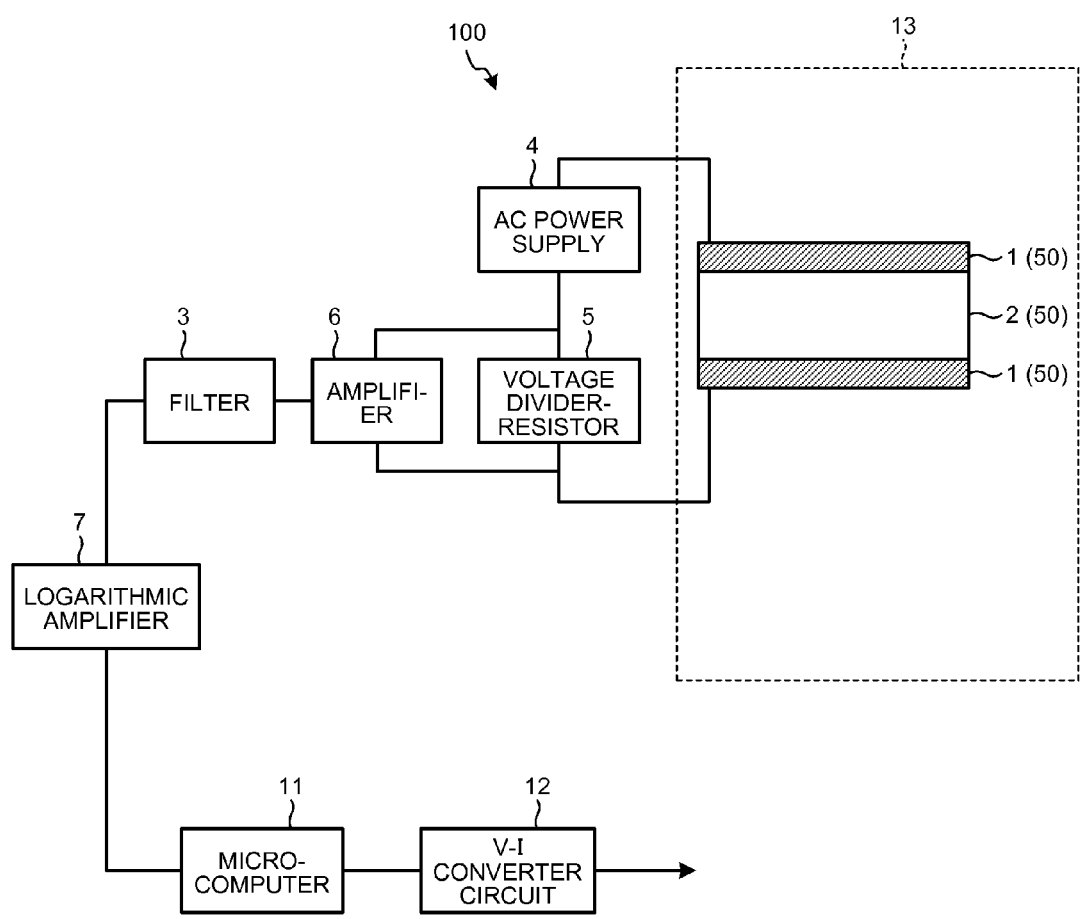
FIG. 1 is a configuration diagram of a water-concentration detection device according to a first embodiment of the present invention.

FIG. 1 is a configuration diagram of a water-concentration detection device according to a first embodiment of the present invention. As shown in FIG. 1, a water-concentration detection device 100 that detects a water concentration of $SF_6$ gas includes an impedance element 50, an AC power supply 4, a voltage divider-resistor 5, an amplifier 6, a filter 3, a logarithmic amplifier 7, a microcomputer (water-concentration detection unit) 11, and a V-I converter circuit 12.

The impedance element 50 is configured to include porous electrodes 1 and a solid electrolyte membrane 2. Specifically, the solid electrolyte membrane 2 is provided between the porous electrodes 1 provided to face each other. The solid electrolyte membrane 2 is fixedly attached to the porous electrodes 1.

The impedance element 50 is installed in a gas-insulated device 13 filled with $SF_6$ gas. The AC power supply 4, the voltage divider-resistor 5 and the amplifier 6 are provided in the outside of the gas-insulated device 13 and connected to the porous electrodes 1 by lead wires.

The porous electrodes 1 are formed on both ends of the solid electrolyte membrane 2, respectively, formed by, for example, subjecting platinum to electroless plating, and have microscopically porous property. The solid electrolyte membrane 2 is made of hydrogen-ion conductive polymer and a water content ratio of the solid electrolyte membrane 2 is in equilibrium with a water concentration of the $SF_6$ gas. That is, the water content ratio increases with increase in the water concentration of the $SF_6$ gas, and the water content ratio decreases with decrease in the water concentration of the $SF_6$ gas. For example, NAFION® manufactured by Du Pont can be used as the solid electrolyte membrane 2.

The AC power supply 4 (voltage application unit) includes an oscillation circuit, converts input direct-current (DC) power supply into an AC voltage of a frequency of 325 Hz, and applies the AC voltage to the porous electrodes 1. An AC voltage value is assumed as a low voltage (about 10 mV to about 1 V) enough not to cause electrolysis of water.

An AC impedance of the solid electrolyte membrane 2 is calculated from a voltage between both ends of the voltage divider-resistor 5, which is measured by the amplifier 6. The reason why the porous electrodes 1 having porous properties are used is because water contained in the $SF_6$ gas can easily permeate the solid electrolyte membrane 2.

Now the description will be made for an operation principle of the water-concentration detection device configured as described above and present in the $SF_6$ gas. The solid electrolyte membrane 2 is in equilibrium with the water contained in the $SF_6$ gas and the water content ratio of the solid electrolyte membrane 2 is in equilibrium with the water concentration of the $SF_6$ gas. On the other hand, the AC impedance of the solid electrolyte membrane 2 changes depending on the water content ratio.

Figure 2:
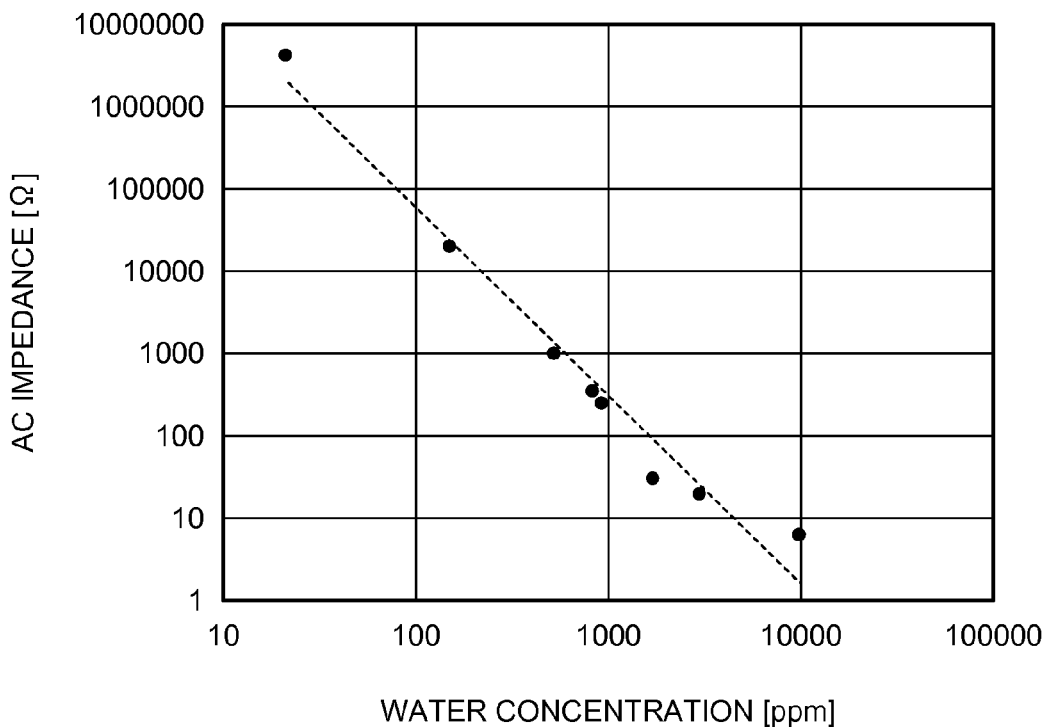
FIG. 2 is a chart showing a relation between a water concentration of $SF_6$ gas and an AC impedance.

FIG. 2 is a chart showing a relation between the water concentration of the $SF_6$ gas and the AC impedance. As shown in FIG. 2, the AC impedance monotonically decreases as the water concentration of the $SF_6$ gas increases and monotonically increases as the water concentration thereof decreases.

Because an electric resistance of the voltage divider-resistor 5 provided in the outside is constant and the AC impedance of the solid electrolyte membrane 2 changes correspondingly to the water concentration in the gas-insulated device 13, the voltage between the both ends of the voltage divider-resistor 5 changes according to the water concentration of the $SF_6$ gas. Therefore, to recognize a change in the AC impedance, the amplifier 6 amplifies the voltage between the both ends of the voltage divider-resistor 5 and outputs the amplified voltage. As can be understood, the voltage divider-resistor 5 and the amplifier 6 function as an impedance measurement unit.

The AC voltage outputted from the amplifier 6 is passed through the filter 3. The filter 3 is a high-pass filter that suppresses passage of frequency components of predetermined frequencies of 50 Hz and 60 Hz, for example, frequency components of 300 Hz or lower. The use of such a high-pass filter can suppress the passage of unnecessary frequency components while allowing frequency components of 325 Hz that is a frequency of the AC voltage applied from the AC power supply 4 to be passed through the filter 3. The AC voltage having passed through the filter 3 is inputted to the logarithmic amplifier 7.

The logarithmic amplifier 7 logarithmically converts the input AC voltage into a DC voltage that falls within an input range of the microcomputer 11. The microcomputer 11 outputs a voltage signal according to a water amount from a D/A conversion terminal. The V-I converter circuit 12 converts the voltage signal outputted from the microcomputer 11 into a current signal of 4 to 12 mA and transmits the obtained current signal to an information collection device (not shown). By transmitting the signal in the form of an electrical current signal, it is possible to transmit the signal more reliably even if the information collection device is set at a distant location.

Figure 3:
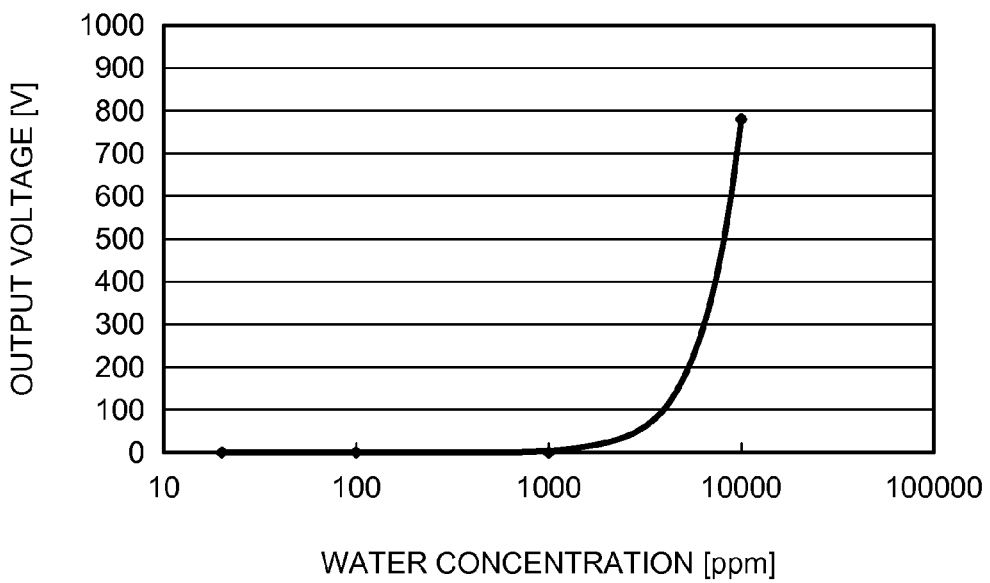
FIG. 3 is a chart showing a relation between a water concentration of $SF_6$ gas and an output voltage in linear scale.

FIG. 3 is a chart showing a relation between the water concentration of the $SF_6$ gas and an output voltage in linear scale. Because of an inverse relation between the voltage on the voltage divider-resistor 5 and the AC impedance, the relation between the water concentration of the $SF_6$ gas and the output voltage is as shown in FIG. 3.

In this way, also between the water concentration of the $SF_6$ gas and the output voltage, there exists a relation that the output voltage monotonically increases as the water concentration of the $SF_6$ gas increases. However, the increase of the output voltage is exponential increase and the number of digits of each of the AC impedance and the output voltage increases by about seven digits according to the water concentration as shown in FIGS. 2 and 3. Therefore, in an example shown in FIG. 3, resolution becomes insufficient in a water concentration equal to or lower than 1000 ppm and it is difficult to accurately discriminate the water concentrations.

In connection thereto, the logarithmic amplifier 7 is used in the first embodiment. It is preferable that the logarithmic amplifier 7 has an input range equal to or higher than 140 dB because the number of digits of each of the AC impedance and the output voltage changes by about seven.

Figure 4:
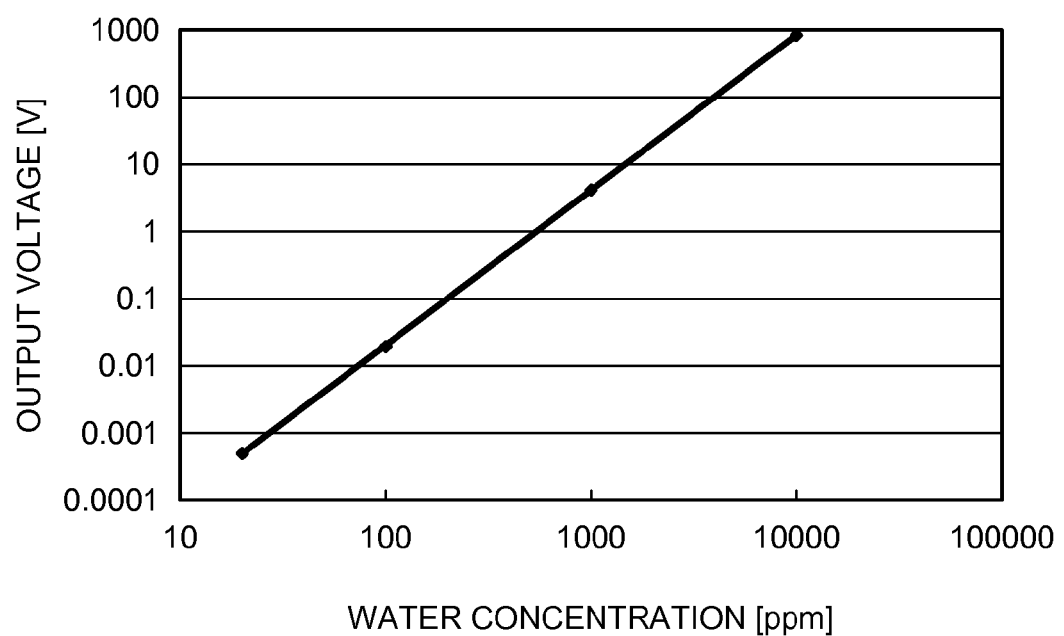
FIG. 4 is a chart showing a relation between a water concentration of $SF_6$ gas and an output voltage obtained by a logarithmic conversion by a logarithmic amplifier.

FIG. 4 is a chart showing a relation between the water concentration of the $SF_6$ gas and the output voltage obtained by a logarithmic conversion by the logarithmic amplifier 7. Because the logarithmic amplifier 7 logarithmically converts the input AC voltage, it is possible to obtain sufficiently high resolution even in the water concentration equal to or lower than 1000 ppm as shown in FIG. 4. Therefore, the water concentration can be measured with higher accuracy in a wide range of water concentrations.

Furthermore, by setting the frequency of the AC voltage applied from the AC power supply 4 to 325 Hz, when the frequency of the commercial power supply is 50 Hz or 60 Hz, degrading of water-concentration measurement accuracy due to the influence of the frequency components thereof can be suppressed.

Further, by setting the frequency of the AC voltage to 325 Hz, a difference of 25 Hz can be given between 300 Hz that is a least common multiple of 50 Hz and 60 Hz and 350 Hz that is a lowest harmonic exceeding 300 Hz. This can suppress the influence of the frequency components that are harmonics of 50 Hz and 60 Hz. The water concentration can be measured with higher accuracy by suppressing the influence of the frequency components that are the harmonics.

Furthermore, the lowest frequency which is equal to or higher than 60 Hz and by which the difference of 25 Hz can be given between the lowest frequency and the harmonics is 325 Hz. In this way, by selecting a lower frequency, the impedance caused by a capacitor component of the solid electrolyte membrane 2 can be measured while being hardly influenced. It is thereby possible to measure the water concentration with much higher accuracy.

It is assumed that the frequency of a commercial power supply is 50 Hz or 60 Hz in the circumstances that the frequency of the AC voltage to be applied from the AC power supply 4 is selected. This results from the consideration that the frequency of a commercial power supply is generally often 50 Hz or 60 Hz.

For example, in Japan, the frequency of a commercial power supply is either 50 Hz or 60 Hz depending on regions. As described in the first embodiment, by setting the frequency of the AC voltage applied from the AC power supply 4 to 325 Hz, the water concentration can be measured with high accuracy while suppressing the influence of the frequency components of the commercial power supply even in regions using their different frequencies.

A frequency of a commercial power supply also differs among countries and the frequency is 50 Hz or 60 Hz. In this case, similarly to the above, by setting the frequency of the AC voltage to be applied from the AC power supply 4 to 325 Hz, the water concentration can be measured with high accuracy while suppressing the influence of the frequency components of the commercial power supply even when the water-concentration detection device 100 is used in a country where the frequency of the commercial power supply is 50 Hz and even when the water-concentration detection device 100 is used in a country where the frequency of the commercial power supply is 60 Hz.

Therefore, there is no need to use different frequencies of the AC voltage to be applied from the AC power supply 4 depending on the regions or countries where the water-concentration detection device 100 is used, so that it is possible to make applied components and products commonalized and to hold down the manufacturing cost of the water-concentration detection device 100.

Alternatively, the frequency of the AC voltage to be applied from the AC power supply 4 may be set to be equal to or lower than 10 Hz that is lower than 50 Hz. By selecting a frequency that is equal to or lower than 10 Hz, it is possible to sufficiently secure a difference from the frequencies of 50 Hz and 60 Hz and, therefore, possible to measure the water concentration with higher accuracy. In this case, as the filter 3, a low-pass filter that suppresses the passage of, for example, frequency components of a frequency equal to or higher than 40 Hz can be used.

A logarithmic amplifier having a narrower input range than 140 dB can be used with an amplification degree of the amplifier 6 being changed.

Second Embodiment

A water concentration of an actually used gas-insulated device is generally several tens of ppm to several hundreds of ppm. When the water concentration decreases to several tens of ppm, the above-mentioned AC impedance of the solid electrolyte membrane increases exponentially from about 10 ohms to become equal to or higher than 1 megaohm with the decrease in the water concentration (see Patent Literature 1).

Generally, an internal temperature of the gas-insulated device installed outdoors changes by as much as several tens of degrees centigrade. It has been known that the water content ratio of the solid electrolyte membrane (NAFION® manufactured by Du Pont, for example) has temperature characteristics in which the impedance becomes lower for the reason that the water content ration becomes higher as the temperature is higher (see Non Patent Literature 1). However, conversely, it is found out that this solid electrolyte membrane has a tendency that, when it has a value lower than a certain water concentration, the impedance becomes higher as the temperature is higher.

However, the conventional water-concentration detection device for detecting the water concentration of the $SF_6$ gas has a problem that a measurement result of the water concentration includes an error due to the ignorance of temperature dependence without consideration to the temperature characteristics of the solid electrolyte membrane.

In the present embodiment, a water-concentration detection device that can reduce a measurement error in the water concentration by taking into account the temperature characteristics of the solid electrolyte membrane at the time of detecting the water concentration is described below.

Figure 5:
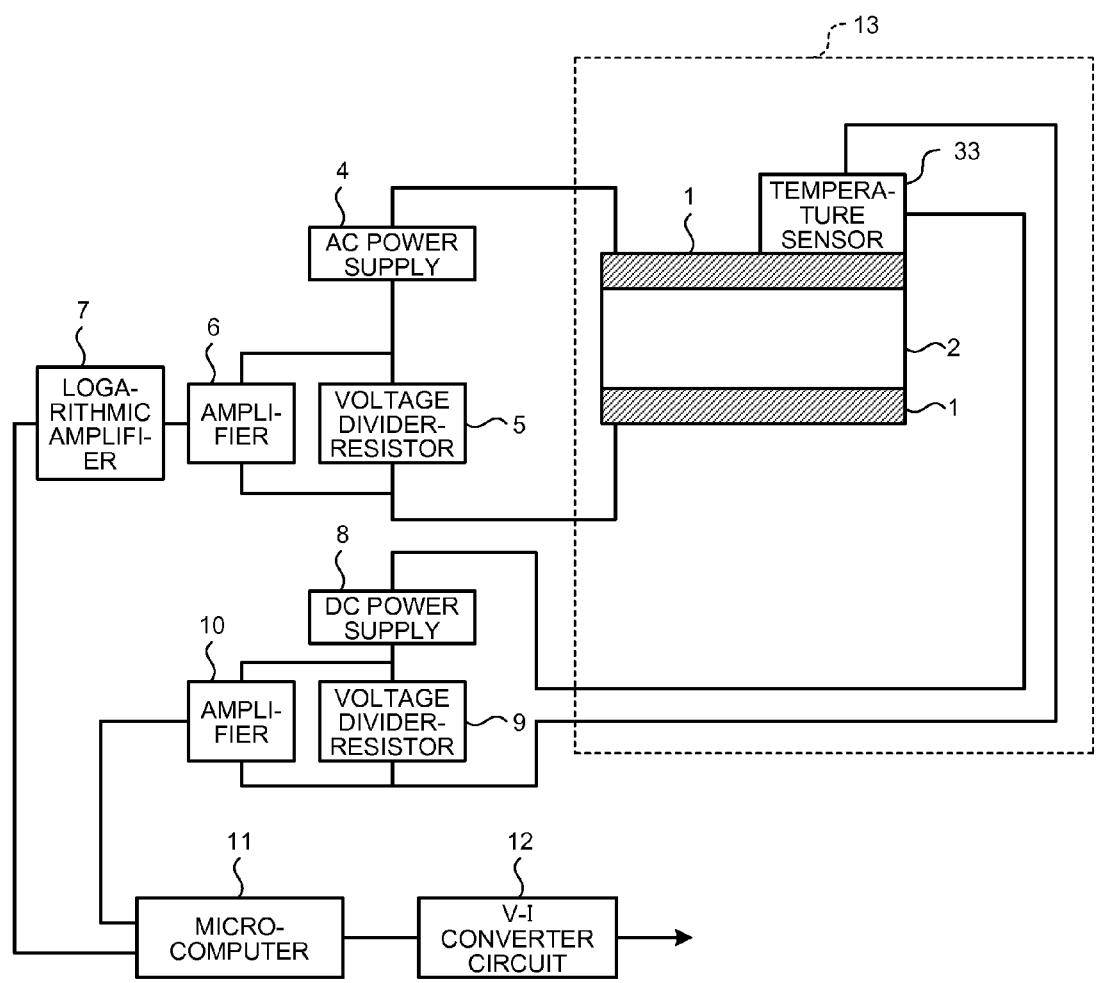
FIG. 5 is a configuration diagram of a water-concentration detection device according to a second embodiment.

FIG. 5 is a configuration diagram of a water-concentration detection device according to the present embodiment. As shown in FIG. 5, the solid electrolyte membrane 2 fixedly attached to the porous electrodes 1 is held between the porous electrodes 1 arranged to face each other and having the porous properties. A temperature sensor 33 is attached to, for example, one of the porous electrodes 1 facing each other. The temperature sensor 33 is configured to include a resistance temperature detector such as a Pt100 (platinum resistor).

The porous electrodes 1, the solid electrolyte membrane 2, and the temperature sensor 33 are arranged within the gas-insulated device 13. A high-voltage conductor (not shown) is accommodated in a cylindrical metal container in the gas-insulated device 13, and the gas-insulated device 13 is filled with insulating gas such as $SF_6$ gas.

The porous electrodes 1 are formed by, for example, subjecting platinum to electroless plating and are microscopically porous. Using the porous electrodes 1 having the porous properties as the electrodes, it is possible to facilitate permeation of water contained in the $SF_6$ gas into the solid electrolyte membrane 2. The solid electrolyte membrane 2 is formed of, for example, hydrogen-ion conductive polymer and the water content ratio of the solid electrolyte membrane 2 is in equilibrium with the water concentration of the $SF_6$ gas. That is, the water content ratio increases with the increase in the water concentration of the $SF_6$ gas, and conversely the water content ratio decreases with the decrease in the water concentration thereof. For example, NAFION® manufactured by Du Pont can be used as the solid electrolyte membrane 2. The porous electrodes 1 and the solid electrolyte membrane 2 constitute an impedance element. Furthermore, because the temperature sensor 33 is attached to the porous electrode 1, a gas temperature near the solid electrolyte membrane 2 can be measured. An installation position of the temperature sensor is not limited to that shown in FIG. 5 as long as it is near the solid electrolyte membrane 2.

The AC power supply 4 that applies a voltage to the porous electrodes 1, the voltage divider-resistor 5 that detects an AC current flowing in the solid electrolyte membrane 2, the amplifier 6 that detects and amplifies an AC voltage across the voltage divider-resistor 5, and the logarithmic amplifier 7 that logarithmically converts an output from the amplifier 6 to convert an AC voltage into a DC voltage are provided in the outside of the gas-insulated device 13. The AC power supply 4, the voltage divider-resistor 5, the amplifier 6, and the logarithmic amplifier 7 constitute an impedance measurement unit that measures an AC impedance between the porous electrodes 1 (that is, an AC impedance of the solid electrolyte membrane 2) by applying the AC voltage to the porous electrodes 1.

A DC power supply 8 that applies a voltage to the temperature sensor 33, a voltage divider-resistor 9 that detects a current flowing in the temperature sensor 33, and an amplifier 10 that detects and amplifies a voltage across the voltage divider-resistor 9 are provided in the outside of the gas-insulated device 13. The temperature sensor 33, the DC power supply 8, the voltage divider-resistor 9, and the amplifier 10 constitute a temperature measurement unit that measures the temperature of insulating gas near the solid electrolyte membrane 2.

The microcomputer 11 connected to the logarithmic amplifier 7 and the amplifier 10 and the V-I converter circuit 12 connected to the microcomputer 11 are provided in the outside of the gas-insulated device 13. The microcomputer 11 includes A/D and D/A conversion terminals, obtains a water concentration of $SF_6$ gas using outputs from the logarithmic amplifier 7 and the amplifier 10 as inputs, and outputs an analog voltage corresponding to this water concentration. The microcomputer 11 constitutes a water-concentration detection unit. The V-I converter circuit 12 converts an output voltage from the microcomputer 11 into a current. That is, the V-I converter circuit 12 converts a voltage signal into a current signal so as to be able to transmit the measurement result of the water concentration to a distant location.

Next, an operation according to the present embodiment is described. First, the water amount of the solid electrolyte membrane 2 is in equilibrium with water contained in the $SF_6$ gas within the gas-insulated device 13. Furthermore, the AC impedance of the solid electrolyte membrane 2 changes depending on the temperature and the water amount.

The AC impedance of the solid electrolyte membrane 2 can be obtained from the voltage generated in the AC power supply 4 and the voltage across the voltage divider-resistor 5. That is, the AC impedance of the solid electrolyte membrane 2 can be obtained by detecting the voltage between the both ends of the voltage divider-resistor 5 because the AC impedance of the solid electrolyte membrane 2 changes according to the water concentration of the $SF_6$ gas and the voltage between the both ends of the voltage divider-resistor 5 also changes according to the water concentration of the $SF_6$ gas. The voltage across the voltage divider-resistor 5 is amplified by the amplifier 6, logarithmically converted by the logarithmic amplifier 7, and converted into the DC voltage that can fall within an input range of the microcomputer 11.

On the other hand, the temperature can be obtained from the voltage generated in the DC power supply 8 and the voltage across the voltage divider-resistor 9. The voltage across the voltage divider-resistor 9 is amplified by the amplifier 10 and converted into the DC voltage that can fall within the input range of the microcomputer 11.

Figure 6:
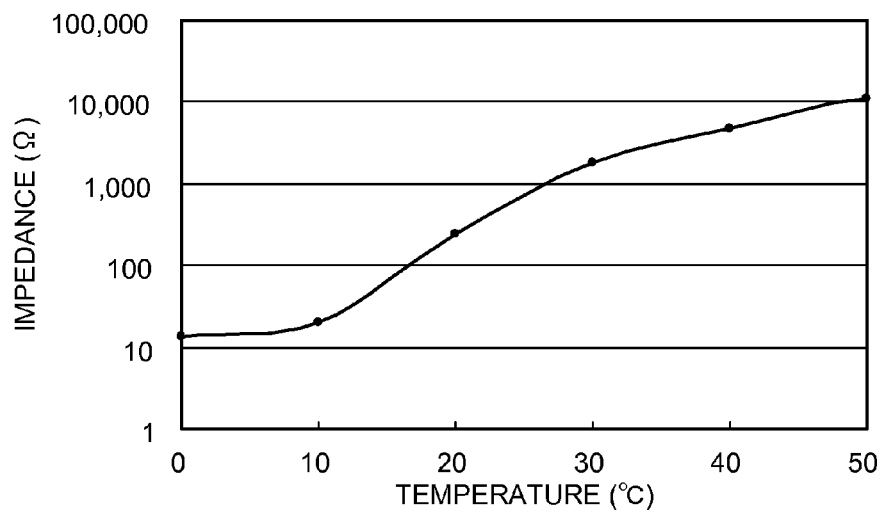
FIG. 6 is a graph showing measurement results of a temperature and an AC impedance in a specific water environment.

When the water amount is large, the solid electrolyte membrane 2 shows generally known behavior of NAFION® and temperature characteristics that the AC impedance becomes lower as the temperature is higher as described in Non Patent Literature 1. On the other hand, when the water amount is small, the solid electrolyte membrane 2 shows temperature characteristics that the AC impedance becomes higher as the temperature is higher as shown in FIG. 6. FIG. 6 is a graph showing measurement results of the temperature and the AC impedance in a specific water environment.

Figure 7:
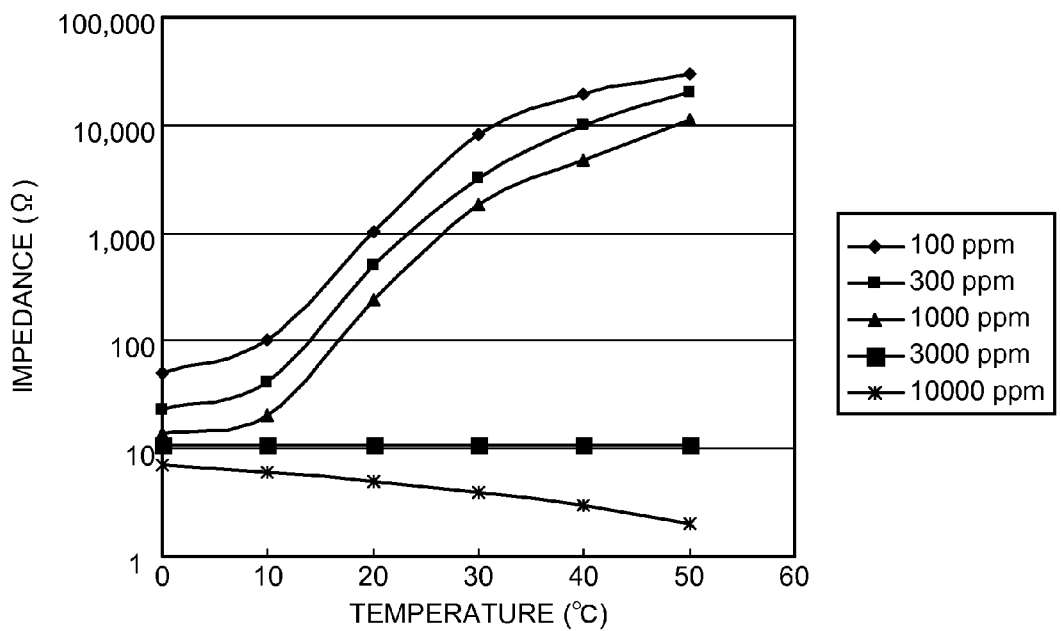
FIG. 7 is a graph showing a relation between an impedance and a water concentration versus a temperature, measured in a test.
Figure 8:
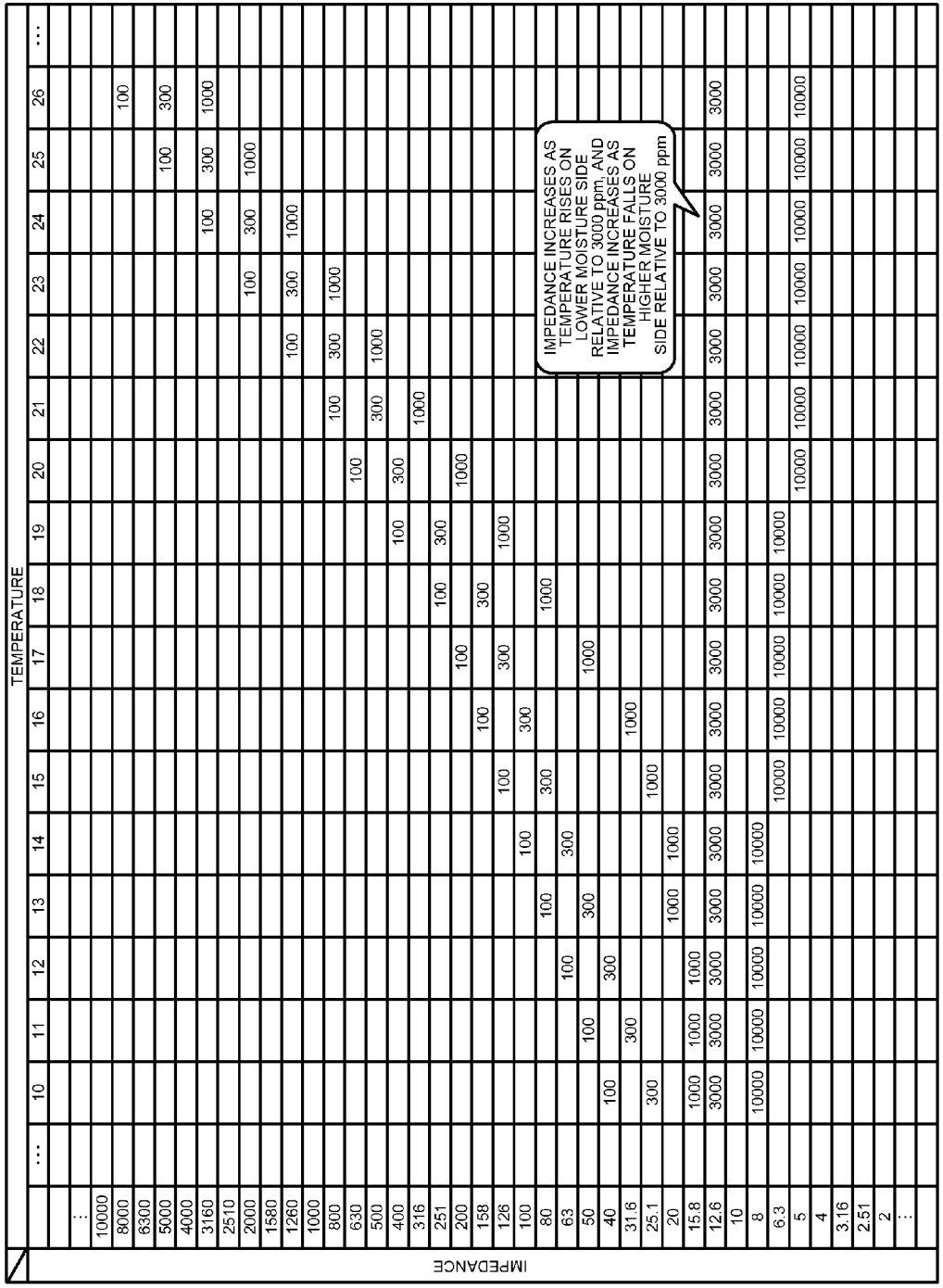
FIG. 8 is a chart showing an example of a matrix in which a water concentration is made to correspond to a temperature and an AC impedance.

FIG. 7 is a graph showing a relation between a temperature versus impedance measured in a test and a water concentration. In FIG. 7, a horizontal axis indicates the temperature (° C.), a vertical axis indicates the impedance (Ω), and five different curves represent cases where the water concentration is 100 (ppm), 300 (ppm), 1000 (ppm), 3000 (ppm) and 10000 (ppm), respectively. A matrix for obtaining a water concentration from temperature information and impedance information measured in the test in advance is stored in the microcomputer 11. FIG. 8 is a chart showing an example of a matrix in which a water concentration is caused to correspond to the temperature and the impedance. FIG. 8 corresponds to a representation obtained by discretizing the graph of FIG. 7, in which a water concentration is given for the discretized impedance and the discretized temperature. In water concentrations lower than 3000 (ppm), the impedance increases as the temperature rises. In water concentrations higher than 3000 (ppm), the impedance decreases as the temperature rises. The microcomputer 11 holds data of the matrix created based on the measurements as shown in FIG. 8 in a storage unit of the microcomputer 11 in advance. When obtaining impedance information and temperature information from the logarithmic amplifier 7 and the amplifier 10, respectively, the microcomputer 11 can detect the water concentration from the obtained temperature information and impedance information by referring to the matrix data.

The microcomputer 11 outputs a voltage signal corresponding to the detected water concentration from its D/A conversion terminal. The V-I converter circuit 12 converts the voltage signal outputted from the microcomputer 11 into a current signal of, for example, 4 to 20 mA and transmits the current signal to a distant information collection device (not shown).

In this way, in the present embodiment, the water concentration is detected by measuring the AC impedance of the solid electrolyte membrane 2 and the gas temperature near the solid electrolyte membrane 2. At that time, the water concentration is detected using the matrix obtained in advance based on the measurement results of the AC impedance and the measurements of the temperature. Therefore, according to the present embodiment, it is possible to reduce a measurement error in the water concentration because the water concentration can be accurately measured without being subjected to the influence of the temperature.

In the present embodiment, the matrix data (table data) in which a water concentration is allocated to the impedance and the temperature is prepared in advance so as to obtain the water concentration in view of the temperature characteristics of the solid electrolyte membrane 2, and the water concentration is obtained by referring to this matrix data. However, a method for obtaining a water concentration is not limited by use of the matrix, and any means may be used as long as a water concentration is allocated to correspond to the impedance and the temperature, and the allocation may be made by, for example, a function.

In the present embodiment, an output of the microcomputer 11 is connected to the V-I converter circuit 12 on the assumption of online monitoring. Alternatively, an offline device can be configured by directly connecting the microcomputer 11 in place of the V-I converter circuit 12 to a display device (not shown).

The present embodiment can be combined with the first embodiment. Specifically, it is sufficient to use the AC power supply 4 shown in FIG. 1 as the AC power supply 4 in FIG. 5. Furthermore, in FIG. 5, the filter 3 shown in FIG. 1 can be provided between the amplifier 6 and the logarithmic amplifier 7. The combination of the present embodiment with the first embodiment makes it possible to measure the water concentration with high accuracy while suppressing the error deriving from the temperature characteristics and also suppressing the influence of the frequency components of a commercial power supply and the frequency components that are the harmonics thereof.

Third Embodiment

In general, the water concentration of insulating gas in an actually used gas-insulated device is several tens of ppm to several hundreds of ppm. Therefore, the water sensor described above is placed in this environment. In this case, when the water concentration decreases from several hundreds of ppm to several tens of ppm, the AC impedance of the solid electrolyte membrane increases exponentially from about 10 ohms to reach 1 megaohm or higher with decrease in the water concentration (see Patent Literature 1).

On the other hand, in an atmospheric environment, the water concentration is equal to or higher than several tens of thousands of ppm and greatly differs from the water concentration within the gas-insulated device. For this reason, for example, when the solid electrolyte membrane for the water sensor having been in equilibrium with the water concentration of the atmospheric environment before a measurement is placed within the gas-insulated device, it takes a considerably long time until this solid electrolyte membrane reaches a state of equilibrium with the water concentration between several tens of ppm and several hundreds of ppm within the gas-insulated device, and it takes a few hours to a few days or more until the water sensor indicates a certain measurement value. As a result, there is a problem that it is impossible to obtain a measurement result in a short time.

In the present embodiment, a water-concentration detection device that can detect a water concentration in a short time is described below.

Figure 9:
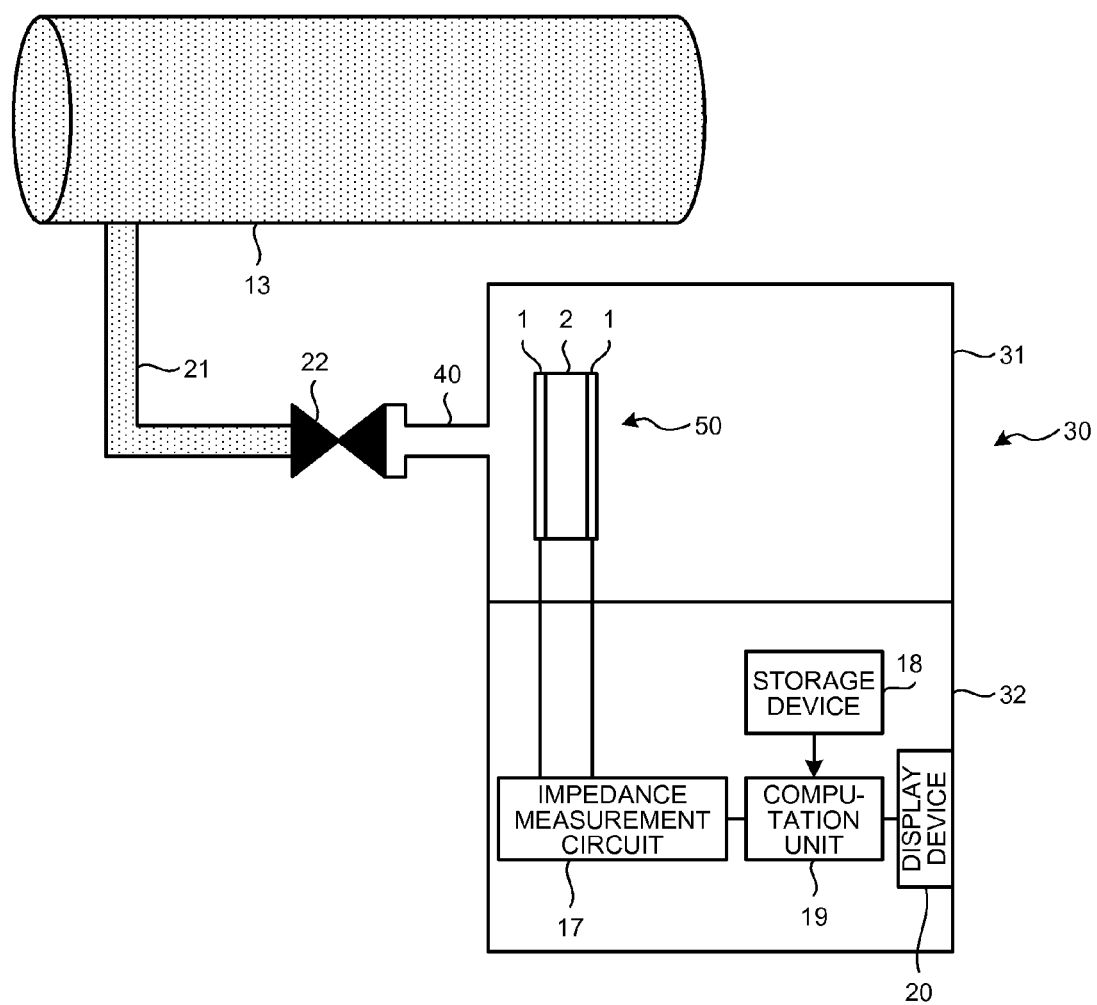
FIG. 9 is a configuration diagram of a water-concentration detection device according to a third embodiment.

FIG. 9 is a configuration diagram of a water-concentration detection device according to the present embodiment. FIG. 9 depicts the gas-insulated device 13 filled with insulating gas such as $SF_6$ gas and a water-concentration detection device 30 attached to this gas-insulated device 13. Specifically, the water-concentration detection device 30 is connected to the gas-insulated device 13 by attaching an attachment port 40 to a piping 21 of the gas-insulated device 13 via a valve 22. When the valve 22 is opened, the insulating gas within the gas-insulated device 13 is introduced into the water-concentration detection device 30 through the piping 21 and used as sampling gas.

The water-concentration detection device 30 is, for example, a portable device and composed of a gas chamber 31 and a signal processing unit 32. The gas chamber 31 is connected to the gas-insulated device 13 via the piping 21 and the valve 22, and the insulating gas introduced from the gas-insulated device 13 by opening the valve 22 can be encapsulated in the gas chamber 31. The paired porous electrodes 1 arranged to face each other and having the porous properties and the solid electrolyte membrane 2 held between and fixedly attached to the porous electrodes 1 are disposed within the gas chamber 31.

The porous electrodes 1 are formed by, for example, subjecting platinum to electroless plating and are microscopically porous. By virtue of use of the porous electrodes 1 as the electrodes, it is possible to facilitate permeation of water contained in the insulating gas into the solid electrolyte membrane 2. The solid electrolyte membrane 2 is formed of, for example, hydrogen-ion conductive polymer and the water content ratio of the solid electrolyte membrane 2 is in equilibrium with the water concentration of the insulating gas. That is, the water content ratio increases with the increase in the water concentration of the insulating gas, and conversely decreases with the decrease in the water concentration of the insulating gas. For example, NAFION® manufactured by Du Pont can be used as the solid electrolyte membrane 2. As described later, the porous electrodes 1 and the solid electrolyte membrane 2 constitute the impedance element 50 that serves as a water sensor that detects the water concentration of the insulating gas.

An impedance measurement circuit 17, a computation unit 19, a display device 20, and a storage device 18 are provided in the signal processing unit 32.

Figure 10:
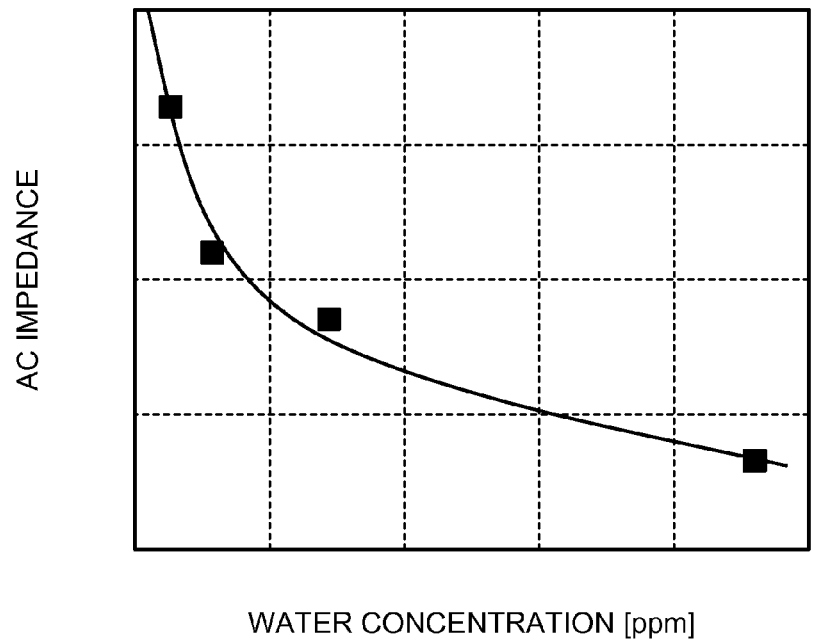
FIG. 10 is a graph showing an example of a relation between a water concentration of insulating gas and an AC impedance of a solid electrolyte membrane.

The impedance measurement circuit 17 is connected to the porous electrodes 1 and measures the AC impedance between the porous electrodes 1 (that is, the AC impedance of the solid electrolyte membrane 2) by applying an AC voltage to the porous electrodes 1 (impedance measurement unit). The impedance measurement circuit 17 outputs a measured value of the impedance to the computation unit 19. FIG. 10 is a graph showing a relation between the water concentration (ppm) of the insulating gas and the AC impedance ($\Omega$) of the solid electrolyte membrane 2 and is created based on the measurement results. As shown in FIG. 10, the AC impedance monotonically decreases as the water concentration increases.

The impedance measurement circuit 17 is configured to include, for example, an AC power supply (not shown) that applies a voltage to the porous electrodes 1, a voltage divider-resistor (not shown) that detects an AC current flowing between the porous electrodes 1 in a state in which the voltage is applied from this AC power supply to the porous electrodes 1, and more. Because the details of the configuration have been described, for example, in Patent Literature 1, explanations thereof will be omitted.

The storage device 18 stores therein a group of impedance-time change curves corresponding to the water concentrations of the insulating gas. Each of the impedance-time change curves is a curve obtained by measuring a time change in the AC impedance between the porous electrodes 1 by the impedance measurement circuit 17 after placing the impedance element 50 in the insulating gas, the element 50 having been previously located in, for example, an atmospheric atmosphere. Further, each of the impedance-time change curves is given for every water concentration of the insulating gas, and indicates voltage response characteristics of the impedance element 50 according to the water concentration. Because the water concentration in the gas-insulated device 13 is typically in a range between several tens of ppm and several hundreds of ppm, the impedance-time change curves beforehand obtained for a plurality of different water concentrations at a constant step size to cover this range, for example, are stored in the storage device 18.

Figure 11:
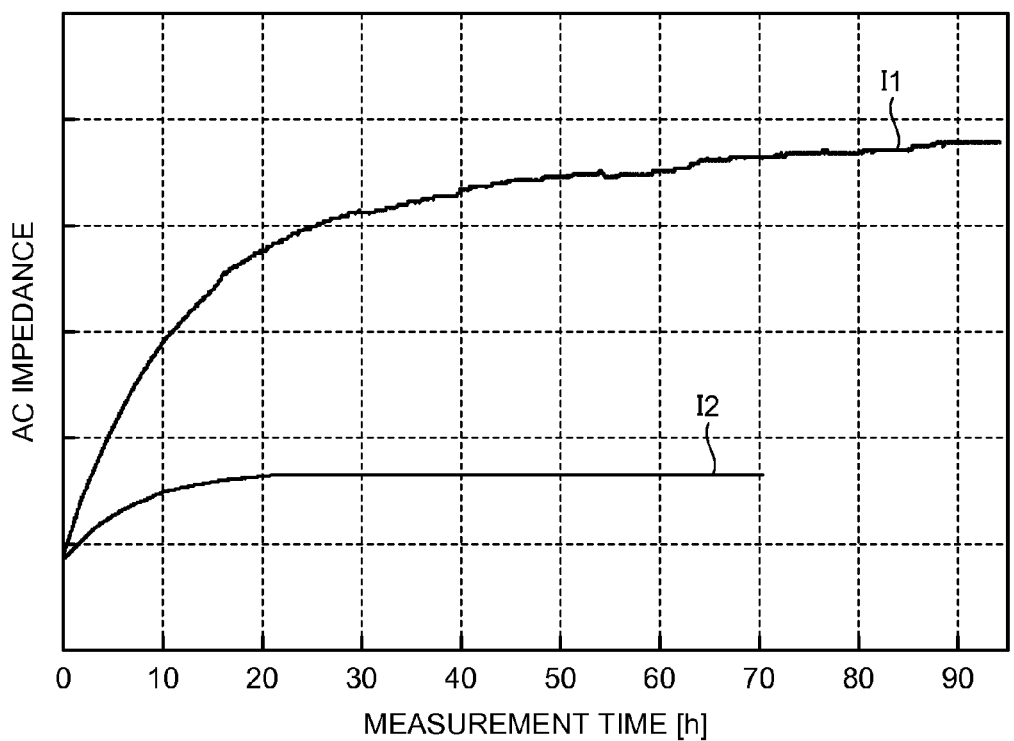
FIG. 11 is a chart showing an example of time change in an impedance of an impedance element.

FIG. 11 is a chart showing an example of the impedance-time change curves. FIG. 11 depicts results obtained in a manner that the impedance element 50 previously located in the atmospheric atmosphere is placed in the insulating gas having a predetermined water concentration and a time change in the AC impedance is measured. In FIG. 11, a curve I1 denotes a measurement result in a case where the water concentration of the insulating gas is several tens of ppm, and a curve I2 denotes a measurement result in a case where the water concentration of the insulating gas is several hundreds of ppm. The storage device 18 stores therein such curves as the curves I1 and I2 shown in FIG. 11 correspondingly to the respective water concentrations in advance.

As can be understood from FIG. 11, the curve I2 in the case where the water concentration of the insulating gas is higher (closer to an atmospheric atmosphere) tends to converge faster and the curve I1 in the case where the water concentration is lower (farther from an atmospheric atmosphere) tends to take a longer time to converge.

In this way, when the water content ratio of the solid electrolyte membrane 2 is close to the water concentration of the measurement-target insulating gas at the time of starting the measurement, a response of the impedance element 50 converges in a short time, but conversely, when the water content ratio is quite different from the water concentration of the insulating gas, the response of the impedance element 50 does not converge for quite some time and it is difficult to promptly obtain a final measurement value. The conventional water-concentration detection device (see Patent Literature 1) waits for the impedance value of the impedance element 50 placed within the insulating gas to converge and determines the water concentration by comparing the convergent value with the water concentration versus AC impedance curve as shown in FIG. 10. Therefore, it took quite a long time to get the water concentration.

The computation unit 19 functions as the water-concentration detection unit. That is, the computation unit 19 compares a behavior of the impedance value before the measured value of the impedance converges after the impedance measurement circuit 17 starts measuring the impedance with the impedance-time change curves stored in the storage device 18, identifies an impedance-time change curve indicating the same behavior as the observed behavior, and outputs the water concentration corresponding to the identified impedance-time change curve as a detected value. That is, the computation unit 19 does not detect the water concentration using a convergent impedance value but estimates the water concentration of the insulating gas at an initial stage after the start of the measurement by comparing the behavior of the impedance value at a time point or during a period before the impedance value converges with the impedance-time change curves stored in the storage device 18 in advance.

The display device 20 can display an output from the computation unit 19. While the water-concentration detection device 30 also includes an input unit for exerting a control or the like over the device and the like, these other constituent elements are omitted in the drawings.

An operation according to the present embodiment is described next. At the time of starting measuring the water concentration, the valve 22 of the piping 21 is opened to allow insulating gas within the gas-insulated device 13 to flow into the gas chamber 31. Before introduction of sampling gas, air in the atmospheric atmosphere, for example, is encapsulated in the gas chamber 31, and the solid electrolyte membrane 2 is in equilibrium with a water concentration of this air. After the insulating gas is introduced into the gas chamber 31, the impedance measurement circuit 17 applies an AC voltage to the porous electrodes 1 and measures an AC impedance according to the water concentration of the solid electrolyte membrane 2. At this time, the measured value of the impedance by the impedance measurement circuit 17 shows the behavior as shown in FIG. 11 correspondingly to the water concentration of the insulating gas because the water amount of the solid electrolyte membrane 2 gradually reaches a state of equilibrium with the water contained in the insulating gas over time. Note that the impedance measurement circuit 17 outputs the measured value of the impedance to the computation unit 19, for example, regularly.

Next, before the impedance value outputted from the impedance measurement circuit 17 converges the computation unit 19 compares at least the behavior of the impedance value at one or more time points or during a certain period of time with the impedance-time change curves stored in the storage device 18, identifies an impedance-time change curve indicating the same behavior as the observed behavior, and outputs a water concentration corresponding to the identified impedance-time change curve as a detected value. That is, the computation unit 19 can estimate the convergent value of the impedance corresponding to the water concentration of the insulating gas and the water concentration itself within predetermined time after the start of the measurement without waiting for a final convergent value from the tendency of the actually measured impedance value as to what time change the impedance shows.

Meanwhile, as shown in FIG. 11, a higher impedance value is shown finally as the water concentration is lower. However, focusing on the initial behavior, the impedance is characterized by rising more sharply as the water concentration is lower and eventually converging into a predetermined impedance value.

In connection thereto, in the present embodiment, the impedance measurement circuit 17 measures an impedance value A [$\Omega$], for example, at a time point when a predetermined measurement time t passes after the start of the measurement. The computation unit 19 compares a point Q constituted by this time t and the impedance value A with the impedance-time change curves and determines on which impedance-time change curve the point Q is present, whereby the computation unit 19 can calculate the water concentration. At this time, in a case where the point Q is not present on any of the impedance-time change curves, the computation unit 19 identifies an impedance-time change curve on which the impedance value at the time t is the closest to the measured value A. The water-concentration detection time can be shortened by making the measurement time t short. Based on the tendency of the impedance to have the time change as shown in FIG. 11, the measurement time t can be set to be equal to or shorter than a few hours, preferably equal to or shorter than 1 hour.

Figure 12:
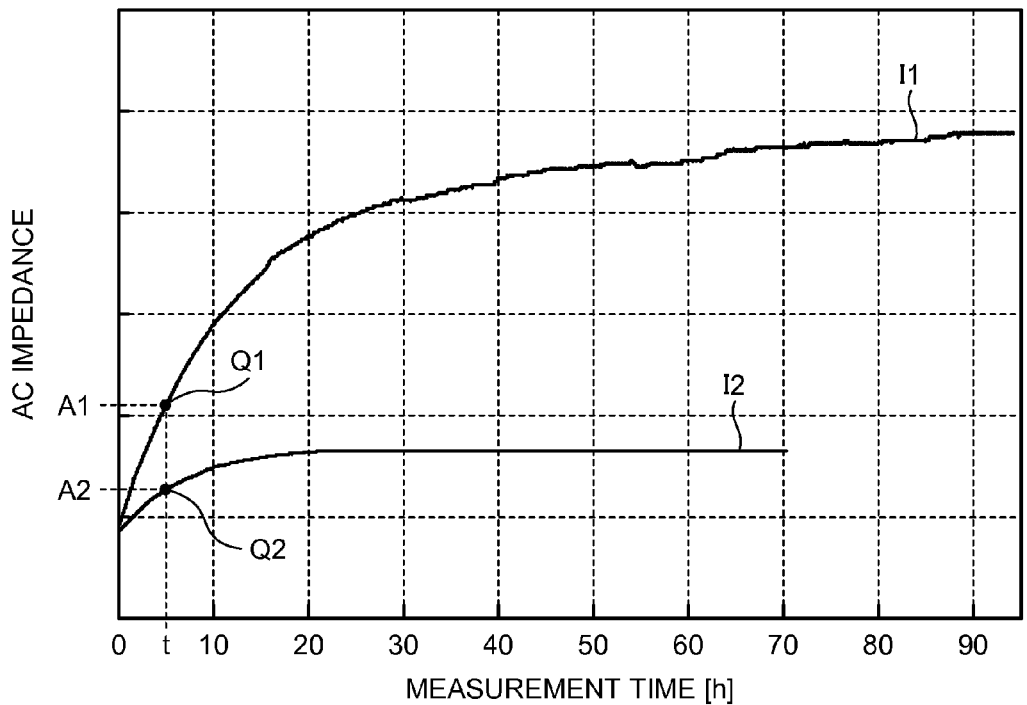
FIG. 12 is a chart showing an example of an impedance value at a time point t on each impedance-time change curve.

FIG. 12 is a chart showing an example of the impedance value at the time point t on each impedance-time change curve. That is, as for the impedance-time change curve I1, the impedance value at the time point t is A1 [$\Omega$] and a corresponding point on the curve is denoted by Q1. As for the impedance-time change curve I2, the impedance value at the time point t is A2 [$\Omega$] and a corresponding point on the curve is denoted by Q2. The computation unit 19 compares a point Q obtained by the measurement with either the point Q1 or Q2 and, when the point Q matches either the point Q1 or Q2 with a measurement error or less, the computation unit 19 can set the water concentration corresponding to the matched curve as a detected value.

In this way, according to the present embodiment, the impedance-time change curves each of which represents how the impedance of the impedance element 50 has the time change are stored for each water concentration of the insulating gas in the storage device 18 in advance, and an initial response characteristic before the measured value of the impedance converges is compared with the impedance-time change curves, thereby to estimate the water concentration before reaching a state of a water adsorption-desorption of the solid electrolyte membrane 2 reaches an equilibrium state. While it conventionally takes, for example, a few hours to a few days or more until the water concentration is deleted, the water concentration can be detected, for example, within about 1 hour according to the present embodiment. Therefore, according to the present embodiment, the water concentration can be measured in a short time.

Fourth Embodiment

In the third embodiment, the water concentration is obtained by measuring the impedance value A [Ω] when, for example, the certain time t passes after the start of the measurement. In the present embodiment, the water concentration is obtained by an initial gradient of the impedance value.

Specifically, by way of example, the water concentration is obtained as follows. The impedance measurement circuit 17 measures the impedance value at a time point of starting the measurement and the impedance value at a time point when the measurement time t passes since the start of the measurement. The computation unit 19 subtracts the impedance value at the time point of the start of the measurement from the impedance value at the time point t and divides a subtraction result by the measurement time t between them, thereby making it possible to calculate a gradient L of the impedance value during a period from the start of the measurement until the measurement time t passes. The computation unit 19 compares this gradient L with the impedance-time change curves, identifies an impedance-time change curve for which a gradient during the period matches or is the closest to the gradient L within a measurement error range, and outputs a water concentration corresponding to the identified impedance-time change curve as a detected value. At this time, similarly to the third embodiment, the water-concentration detection time can be shortened by making the measurement time t short. The period during which the gradient is calculated, described here is only an example and the gradient can be obtained by setting another period.

Figure 13:
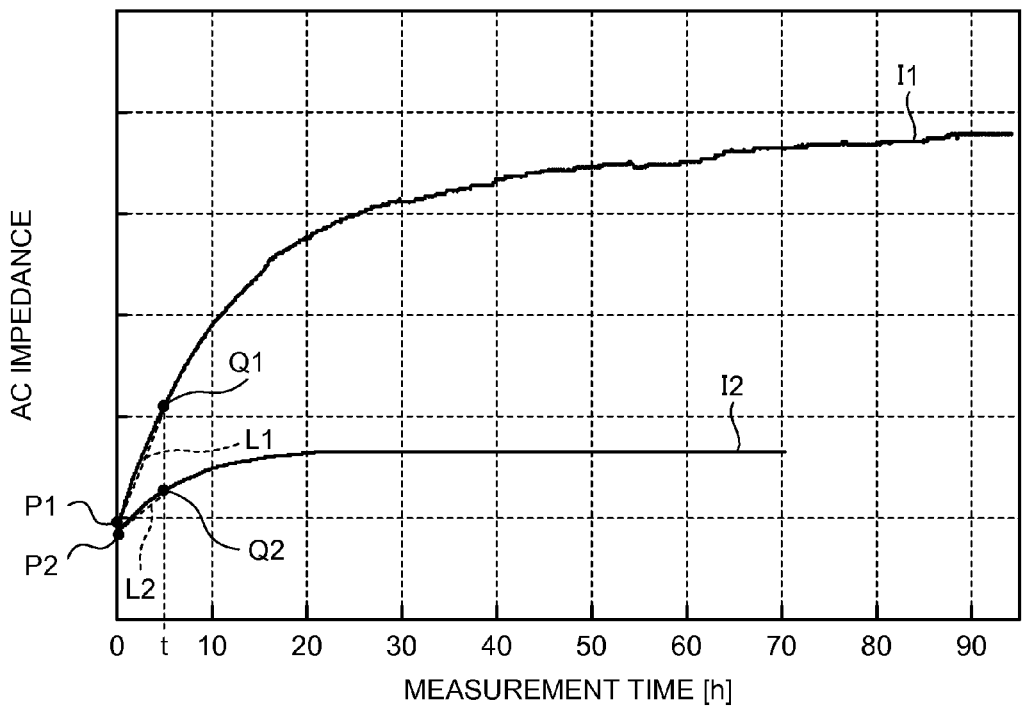
FIG. 13 is a chart showing an example of a slope of an impedance value within a predetermined initial period on each impedance-time change curve.

FIG. 13 is a chart showing an example of the gradient of the impedance value during a predetermined initial period on each impedance-time change curve. That is, as for the impedance-time change curve I1, a point on the curve at a time 0 is P1, a point on the curve at the time t is Q1, and a gradient of a line connecting the Q1 to the P1 is set as L1. As for the impedance-time change curve I2, a point on the curve at the time 0 is P2, a point on the curve at the time t is Q2, and a gradient of a line connecting the Q2 to the P2 is set as L2. The computation unit 19 compares the gradient L obtained by the measurement with either the gradient L1 or L2 and, when the gradient L matches the L1 or L2 with a measurement error or less, the computation unit 19 can set the water concentration corresponding to the matched curve as a detected value.

In the present embodiment, the water concentration is detected by obtaining the gradient from the impedance values at the two time points. Therefore, for example, even when a measurement accuracy of the impedance value at one time point is slightly low and the measurement accuracy in a case of applying the third embodiment is slightly inferior, it is possible to improve the water-concentration detection accuracy by compensating for the measurement accuracy at each time point by virtue of information at the two time points.

Other effects of the present embodiment are identical to those according to the third embodiment.

In the third embodiment, the water concentration is estimated based on the impedance value, for example, at one time point after the start of the measurement. In the fourth embodiment, the water concentration is estimated based on the gradient of the impedance value, for example, during a certain period after the start of the measurement. However, these are simply specific examples of estimating the water concentration according to the present invention. Generally, it is sufficient that the initial behavior of the impedance value is compared with the impedance-time change curves either directly or indirectly and the water concentration is estimated. For example, the water concentration may be estimated by comparing the measured values of the impedance at a plurality of time points, for example three or more time points with the impedance-time change curves.

The third and fourth embodiments can be combined with the first embodiment. Specifically, in FIG. 9, the impedance measurement circuit 17 can be configured to include, for example, the AC power supply 4, the voltage divider-resistor 5, the amplifier 6, the filter 3, and the logarithmic amplifier 7 shown in FIG. 1. Furthermore, the computation unit 19 shown in FIG. 9 corresponds to the microcomputer 11 and the V-I converter circuit 12 shown in FIG. 1. The combination with the first embodiment makes it possible to measure the water concentration with high accuracy and to measure the water concentration in a short time while suppressing the influence of the frequency components of a commercial power supply and the frequency components that are the harmonics thereof.

Figure 14:
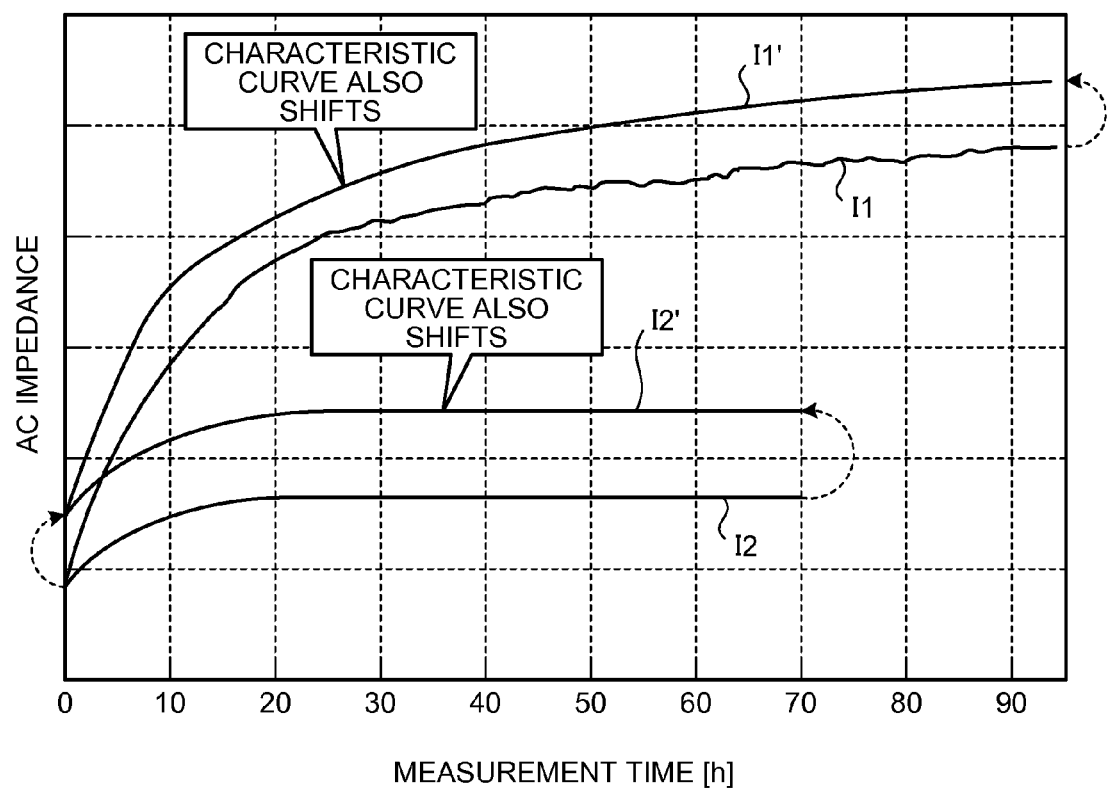
FIG. 14 is a chart showing an example of time change in an impedance of an impedance element with respect to different temperatures.

The third and fourth embodiments can be combined with the second embodiment. Specifically, in FIG. 9, the impedance measurement circuit 17 is configured to include, for example, the AC power supply 4, the voltage divider-resistor 5, the amplifier 6, and the logarithmic amplifier 7 shown in FIG. 5. The temperature sensor 33 shown in FIG. 5 is provided to the porous electrodes 1 within the gas chamber 31, and the temperature measurement unit (the DC power supply 8, the voltage divider-resistor 9, and the amplifier 10) shown in FIG. 5 is provided in the signal processing unit 32. The temperature sensor 33, the DC power supply 8, the voltage divider-resistor 9, and the amplifier 10 are connected similarly to FIG. 5 so as to input the output from the amplifier 10 to the computation unit 19. The computation unit 19 shown in FIG. 9 corresponds to the microcomputer 11 and the V-I converter circuit 12 shown in FIG. 5. In this case, the impedance-time change curves corresponding to the water concentrations and the temperatures of the insulating gas are stored in the storage device 18 for a plurality of different water concentrations and a plurality of different temperatures, respectively. These impedance-time change curves may be stored as matrix data as shown in FIG. 8. FIG. 14 is a chart showing an example of the time change in the impedance of the impedance element at different temperatures. In FIG. 14, the curve I1 indicates a measurement result in a case where the water concentration of the insulating gas at a normal temperature is several tens of ppm, a curve I1' indicates a measurement result in a case where the water concentration of the insulating gas in a high temperature state is several tens of ppm, the curve I2 indicates a measurement result in a case where the water concentration of the insulating gas at a normal temperature is several hundreds of ppm, and a curve I2' indicates a case where the water concentration of the insulating gas in a high temperature state is several hundreds of ppm. The storage device 18 stores such curves as the curves I1, I1', I2 and I2' shown in FIG. 14 for the respective water concentrations in advance. The computation unit 19 compares at least the behavior of the impedance value at one or more time points or during a certain period with the impedance-time change curves corresponding to the measured temperatures stored in the storage device 18 based on the temperature of the insulating gas measured by the temperature measurement unit before the impedance value outputted from the impedance measurement circuit 17 converges, identifies an impedance-time change curve indicating the same behavior as the observed behavior, and outputs a water concentration corresponding to the identified impedance-time change curve as a detected value. The combination with the second embodiment makes it possible to suppress an error resulting from the temperature characteristics and also to measure the water concentration in a short time. It is clear from the above explanations that the third and fourth embodiments can be combined with the first embodiment and the second embodiment.

INDUSTRIAL APPLICABILITY

As described above, the water-concentration detection device according to the present invention is useful for measuring a water concentration of $SF_6$ gas within a gas-insulated device.

REFERENCE SIGNS LIST

1 porous electrode
2 solid electrolyte membrane
3 filter
4 AC power supply
5, 9 voltage divider-resistor
6, 10 amplifier
7 logarithmic amplifier
8 DC power supply
11 microcomputer
12 V-I converter circuit
13 gas-insulated device
17 impedance measurement circuit
18 storage device
20 display device
33 temperature sensor
50 impedance element
100 water-concentration detection device

The invention claimed is:

1. A water-concentration detection device for detecting a water concentration of insulating gas filled in a gas-insulated device, the water-concentration detection device comprising:
    porous electrodes that are arranged to face each other in the insulating gas;
    a solid electrolyte membrane that is sandwiched between and fixedly attached to the electrodes, and has hydrogen-ion conductivity;
    a voltage application unit that applies an alternating-current voltage to the electrodes at a frequency of 325 Hz or a frequency equal to or lower than 10 Hz;
    an impedance measurement unit that measures an alternating-current impedance between the electrodes in a state in which the alternating-current voltage is applied to the electrodes;
    a logarithmic amplifier that logarithmically converts the alternating-current impedance measured by the impedance measurement unit and outputs a conversion result;
    a water-concentration detection unit that detects a water concentration of the insulating gas based on the alternating-current impedance outputted from the logarithmic amplifier;
    a gas chamber in which air in an atmospheric atmosphere is encapsulated before starting measuring the water concentration, in which the insulating gas introduced from the gas-insulated device is encapsulated at a time of starting measuring the water concentration, and inside which the electrodes are arranged to face each other; and
    a storage unit that stores impedance-time change curves for a plurality of different water concentrations, respectively, each of the impedance-time change curves representing a time change in the alternating-current impedance according to the water concentration of the insulating gas, wherein
    the water-concentration detection unit compares at least a behavior of a measured value of the alternating-current impedance at one or more time points or of the measured value of the alternating-current impedance during a certain period with the impedance-time change curves stored in the storage unit before the measured value of the alternating-current impedance obtained by the impedance measurement unit converges, identifies an impedance-time change curve that indicates a same behavior as the behavior, and outputs a water concentration corresponding to the identified impedance-time change curve as a detected value.

2. The water-concentration detection device according to claim 1, wherein the logarithmic amplifier has an input characteristic of 140 dB or higher.

3. The water-concentration detection device according to claim 1, wherein
    the frequency of the alternating-current voltage applied to the electrodes is 325 Hz, and
    the water-concentration detection device further comprises a high-pass filter that removes components of a predetermined frequency or lower including 50 Hz and 60 Hz and passes components of 325 Hz.

4. The water-concentration detection device according to claim 1, comprising a temperature measurement unit that measures a temperature of the insulating gas using a temperature sensor attached to the electrodes, wherein
    the water-concentration detection unit holds data or a function for allocating a water concentration to the temperature and the alternating-current impedance in advance, and detects the water concentration of the insulating gas using the data or the function based on the alternating-current impedance measured by the impedance measurement unit and the temperature measured by the temperature measurement unit.

5. The water-concentration detection device according to claim 1, wherein the water-concentration detection unit holds matrix data for allocating a water concentration to the temperature and the alternating-current impedance in advance, and outputs a water concentration corresponding to the alternating-current impedance measured by the impedance measurement unit and the temperature measured by the temperature measurement unit as a detected value with reference to the matrix data.

6. The water-concentration detection device according to claim 5, wherein in the matrix data, impedance increases as the temperature rises in water concentrations lower than a specific water concentration, and the impedance decreases as the temperature rises in water concentrations higher than the specific water concentration.

7. The water-concentration detection device according to claim 1, wherein the water-concentration detection unit compares the measured value of the alternating-current impedance at a time point at which a predetermined time passes since start of measuring the water concentration with the impedance-time change curves stored in the storage unit, identifies an impedance-time change curve on which a value of the alternating-current impedance at the time point at which the predetermined time passes matches or is closest to the measured value of the alternating-current impedance, and outputs a water concentration corresponding to the identified impedance-time change curve as a detected value.

8. The water-concentration detection device according to claim 7, wherein the water-concentration detection unit compares a gradient of the measured value of the alternating-current impedance during a predetermined period with the impedance-time change curves stored in the storage unit, identifies an impedance-time change curve for which a gradient of the alternating-current impedance during the predetermined period matches or is closest to the gradient of the measured value of the alternating-current impedance, and outputs a water concentration corresponding to the identified impedance-time change curve as a detected value.

9. The water-concentration detection device according to claim 4, wherein the storage unit stores impedance-time change curves for a plurality of different water concentrations and a plurality of different temperatures, respectively, each of the impedance-time change curves representing a time change in the alternating-current impedance according to the water concentration and temperature of the insulating gas, and the water-concentration detection unit compares at least a behavior of a value of an impedance at one or more time points or of the value of the impedance during a certain period with the impedance-time change curves stored in the storage unit and corresponding to the temperature based on the temperature of the insulating gas measured by the temperature measurement unit before the measured value of the alternating-current impedance measured by the impedance measurement unit converges, identifies an impedance-time change curve that indicates a same behavior as the behavior, and outputs a water concentration corresponding to the identified impedance-time change curve as a detected value.

* * * * *